United States Patent
Shuros et al.

(10) Patent No.: US 8,983,600 B2
(45) Date of Patent: Mar. 17, 2015

(54) METHOD AND APPARATUS FOR SAFETY CONTROL DURING CARDIAC PACING MODE TRANSITION

(75) Inventors: Allan C. Shuros, St. Paul, MN (US); Eric A. Mokelke, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 445 days.

(21) Appl. No.: 12/768,925

(22) Filed: Apr. 28, 2010

(65) Prior Publication Data

US 2010/0292745 A1    Nov. 18, 2010

Related U.S. Application Data

(60) Provisional application No. 61/178,799, filed on May 15, 2009.

(51) Int. Cl.
*A61N 1/00*   (2006.01)
*A61N 1/368*   (2006.01)

(52) U.S. Cl.
CPC .............. *A61N 1/368* (2013.01); *A61N 1/3688* (2013.01)
USPC ................................. 607/9; 607/14

(58) Field of Classification Search
USPC ....................................... 607/9, 14
See application file for complete search history.

(56) References Cited

U.S. PATENT DOCUMENTS

| | | | |
|---|---|---|---|
| 4,834,710 A | 5/1989 | Fleck | |
| 5,007,427 A | 4/1991 | Suzuki et al. | |
| 5,072,458 A | 12/1991 | Suzuki | |
| 5,111,818 A | 5/1992 | Suzuki et al. | |
| 5,135,004 A | 8/1992 | Adams et al. | |
| 5,144,949 A * | 9/1992 | Olson | 607/17 |
| 5,184,615 A | 2/1993 | Nappholz et al. | |
| 5,199,428 A | 4/1993 | Obel et al. | |
| 5,282,840 A | 2/1994 | Hudrlik et al. | |
| 5,313,953 A | 5/1994 | Yomtov et al. | |
| 5,484,419 A | 1/1996 | Fleck | |
| 5,531,768 A | 7/1996 | Alferness | |
| 5,540,727 A | 7/1996 | Tockman et al. | |
| 5,919,209 A | 7/1999 | Schouten | |

(Continued)

FOREIGN PATENT DOCUMENTS

| | | |
|---|---|---|
| EP | 1690566 A1 | 8/2006 |
| WO | WO-9518649 A1 | 7/1995 |

(Continued)

OTHER PUBLICATIONS

"International Application Serial No. PCT/US2010/032676, International Search Report mailed Jul. 12, 2010", 4 pgs.

(Continued)

*Primary Examiner* — Michael Kahelin
*Assistant Examiner* — Mallika D Fairchild
(74) *Attorney, Agent, or Firm* — Schwegman Lundberg & Woessner, P.A.

(57) ABSTRACT

A cardiac pacing system introduces a transitional period when pacing mode changes, such as when pacing starts and stops, or when one or more pacing parameter values change substantially. For each pacing parameter that changes substantially when the pacing mode changes, its value is adjusted incrementally over the transitional period to protect the heart from potentially harmful conditions associated with an abrupt change in the value of that pacing parameter.

22 Claims, 8 Drawing Sheets

(56) References Cited

U.S. PATENT DOCUMENTS

| | | | |
|---|---|---|---|
| 5,991,659 A | 11/1999 | de Vries et al. |
| 6,021,350 A | 2/2000 | Mathson |
| 6,108,577 A | 8/2000 | Benser |
| 6,151,525 A | 11/2000 | Soykan et al. |
| 6,256,538 B1 | 7/2001 | Ekwall |
| 6,272,379 B1 | 8/2001 | Fischell et al. |
| 6,278,894 B1 | 8/2001 | Salo et al. |
| 6,285,907 B1 | 9/2001 | Kramer et al. |
| 6,314,323 B1 | 11/2001 | Ekwall et al. |
| 6,368,284 B1 | 4/2002 | Bardy |
| 6,477,402 B1 | 11/2002 | Lynch et al. |
| 6,501,983 B1 | 12/2002 | Natarajan et al. |
| 6,569,145 B1 | 5/2003 | Shmulewitz et al. |
| 6,584,362 B1 | 6/2003 | Scheiner et al. |
| 6,604,000 B2 | 8/2003 | Lu |
| 6,628,988 B2 | 9/2003 | Kramer et al. |
| 6,711,436 B1 | 3/2004 | Duhaylongsod |
| 6,827,690 B2 | 12/2004 | Bardy |
| 6,842,642 B2 | 1/2005 | Vanhout |
| 6,845,267 B2 | 1/2005 | Harrison et al. |
| 6,865,420 B1 | 3/2005 | Kroll |
| 6,913,577 B2 | 7/2005 | Bardy |
| 6,937,899 B2 | 8/2005 | Sheldon et al. |
| 6,950,701 B2 | 9/2005 | Begemann et al. |
| 6,965,797 B2 | 11/2005 | Pastore et al. |
| 6,973,349 B2 | 12/2005 | Salo |
| 7,010,345 B2 | 3/2006 | Hill et al. |
| 7,039,462 B2 | 5/2006 | Pastore et al. |
| 7,062,325 B1 | 6/2006 | Krig et al. |
| 7,069,070 B2 | 6/2006 | Carlson et al. |
| 7,072,711 B2 | 7/2006 | Girouard et al. |
| 7,171,258 B2 | 1/2007 | Goode |
| 7,215,997 B2 | 5/2007 | Yu et al. |
| 7,277,761 B2 | 10/2007 | Shelchuk |
| 7,295,874 B2 | 11/2007 | Prinzen et al. |
| 7,299,087 B2 | 11/2007 | Bardy |
| 7,340,303 B2 | 3/2008 | Zhu |
| 7,364,547 B2 | 4/2008 | Stahmann et al. |
| 7,460,906 B2 | 12/2008 | Libbus |
| 7,479,112 B2 | 1/2009 | Sweeney et al. |
| 7,486,991 B2 | 2/2009 | Libbus et al. |
| 7,668,594 B2 | 2/2010 | Brockway et al. |
| 7,689,279 B2 | 3/2010 | Ziegler et al. |
| 2002/0042632 A1 | 4/2002 | Iaizzo et al. |
| 2002/0072777 A1 | 6/2002 | Lu |
| 2002/0082660 A1 | 6/2002 | Stahmann et al. |
| 2002/0091415 A1* | 7/2002 | Lovett et al. .............. 607/14 |
| 2002/0143369 A1 | 10/2002 | Hill et al. |
| 2003/0004549 A1 | 1/2003 | Hill et al. |
| 2003/0009189 A1 | 1/2003 | Gilson et al. |
| 2003/0045908 A1 | 3/2003 | Condie et al. |
| 2003/0060854 A1 | 3/2003 | Zhu |
| 2003/0120313 A1 | 6/2003 | Begemann et al. |
| 2003/0120315 A1 | 6/2003 | Spinelli et al. |
| 2003/0139778 A1 | 7/2003 | Fischell et al. |
| 2003/0158584 A1 | 8/2003 | Cates et al. |
| 2003/0204206 A1 | 10/2003 | Padua et al. |
| 2003/0204231 A1 | 10/2003 | Hine et al. |
| 2003/0233130 A1 | 12/2003 | Padmanabhan et al. |
| 2004/0015081 A1 | 1/2004 | Kramer et al. |
| 2004/0038947 A1 | 2/2004 | Wink et al. |
| 2004/0088017 A1 | 5/2004 | Sharma et al. |
| 2004/0106960 A1 | 6/2004 | Siejko et al. |
| 2004/0133247 A1 | 7/2004 | Stahmann et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0043675 A1 | 2/2005 | Pastore et al. |
| 2005/0075673 A1 | 4/2005 | Warkentin et al. |
| 2005/0137631 A1 | 6/2005 | Yu et al. |
| 2005/0143779 A1 | 6/2005 | Libbus |
| 2005/0149129 A1 | 7/2005 | Libbus et al. |
| 2005/0171589 A1 | 8/2005 | Lau et al. |
| 2005/0197674 A1 | 9/2005 | McCabe et al. |
| 2005/0261741 A1 | 11/2005 | Libbus et al. |
| 2005/0283195 A1 | 12/2005 | Pastore et al. |
| 2005/0288721 A1 | 12/2005 | Girouard et al. |
| 2006/0030892 A1 | 2/2006 | Kadhiresan et al. |
| 2006/0116593 A1 | 6/2006 | Zhang et al. |
| 2006/0149326 A1 | 7/2006 | Prinzen et al. |
| 2006/0206158 A1 | 9/2006 | Wu et al. |
| 2006/0241357 A1 | 10/2006 | Chirife |
| 2006/0241704 A1 | 10/2006 | Shuros et al. |
| 2006/0247686 A1 | 11/2006 | Girouard et al. |
| 2006/0247700 A1 | 11/2006 | Jackson |
| 2006/0253156 A1 | 11/2006 | Pastore et al. |
| 2006/0259088 A1 | 11/2006 | Pastore et al. |
| 2006/0287684 A1 | 12/2006 | Baynham et al. |
| 2007/0021789 A1 | 1/2007 | Pastore et al. |
| 2007/0043393 A1 | 2/2007 | Brockway et al. |
| 2007/0049835 A1 | 3/2007 | Goode |
| 2007/0054871 A1 | 3/2007 | Pastore et al. |
| 2007/0150005 A1 | 6/2007 | Sih et al. |
| 2007/0150015 A1 | 6/2007 | Zhang et al. |
| 2007/0162081 A1 | 7/2007 | Yu et al. |
| 2007/0179392 A1 | 8/2007 | Zhang |
| 2007/0203524 A1 | 8/2007 | Sheldon et al. |
| 2007/0239218 A1 | 10/2007 | Carlson et al. |
| 2007/0282380 A1 | 12/2007 | Brooke et al. |
| 2007/0288062 A1 | 12/2007 | Stahmann et al. |
| 2007/0299356 A1 | 12/2007 | Wariar et al. |
| 2008/0015649 A1 | 1/2008 | Stroebel |
| 2008/0027495 A1 | 1/2008 | Prinzen et al. |
| 2008/0058661 A1 | 3/2008 | Bardy |
| 2008/0058881 A1 | 3/2008 | Wagner et al. |
| 2008/0081354 A1 | 4/2008 | Qu et al. |
| 2008/0082135 A1 | 4/2008 | Arcot-Krishnamurthy et al. |
| 2008/0091138 A1 | 4/2008 | Pastore et al. |
| 2008/0132972 A1 | 6/2008 | Shuros et al. |
| 2008/0140141 A1 | 6/2008 | Ben-David et al. |
| 2008/0177156 A1 | 7/2008 | Zhang et al. |
| 2008/0177191 A1 | 7/2008 | Patangay et al. |
| 2008/0177194 A1 | 7/2008 | Zhang et al. |
| 2008/0221636 A1 | 9/2008 | Pastore et al. |
| 2009/0025459 A1 | 1/2009 | Zhang et al. |
| 2009/0048641 A1 | 2/2009 | Libbus |
| 2009/0082781 A1 | 3/2009 | Tran et al. |
| 2009/0124916 A1 | 5/2009 | Sweeney et al. |
| 2009/0192560 A1 | 7/2009 | Arcot-Krishnamurthy et al. |

FOREIGN PATENT DOCUMENTS

| | | |
|---|---|---|
| WO | WO-0115609 A1 | 3/2001 |
| WO | WO-2004058326 A2 | 7/2004 |
| WO | WO-2006074189 A1 | 7/2006 |
| WO | WO-2006115693 A2 | 11/2006 |
| WO | WO-2006115693 A3 | 11/2006 |
| WO | WO-2006121842 A2 | 11/2006 |
| WO | WO-2006124636 A2 | 11/2006 |
| WO | WO-2006124636 A3 | 11/2006 |
| WO | WO-2006124729 A2 | 11/2006 |
| WO | WO-2006124729 A3 | 11/2006 |
| WO | WO-2007133962 A2 | 11/2007 |
| WO | WO-2007133962 A3 | 11/2007 |

OTHER PUBLICATIONS

"International Application Serial No. PCT/US2010/032676, Written Opinion mailed Jul. 12, 2010", 8 pgs.

* cited by examiner

METHOD AND APPARATUS FOR SAFETY CONTROL DURING CARDIAC PACING MODE TRANSITION

CROSS-REFERENCE TO RELATED APPLICATION

This application claims the benefit of U.S. Provisional Application No. 61/178,799, filed on May 15, 2009, under 35 U.S.C. §119(e), which is hereby incorporated by reference in its entirety.

TECHNICAL FIELD

This document relates generally to cardiac rhythm management (CRM) systems and particularly to a pacemaker including safety control that protects the heart from potentially harmful conditions associated with abrupt change of pacing parameters during a pacing mode transition.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium (cardiac muscles). In a normal heart, the sinoatrial (SA) node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions.

Cardiac arrhythmia occurs when the heart's electrical activities become abnormal, such as when the SA node fails to generate electrical impulses at a normal rate, when the conduction of the electrical impulses in a portion of the electrical conduction system is blocked or abnormally delayed, when a pathological electrical conduction path form in the heart, and/or when a pathological focus generates electrical impulses to usurp control of the rhythm of the cardiac contractions from the SA node. A blocked or otherwise abnormal electrical conduction and/or deteriorated myocardial tissue cause dyssynchronous contraction of the heart, which may eventually lead to heart failure, a condition in which the heart fails to pump enough blood to meet the body's metabolic needs. Myocardial infarction (MI) is the necrosis of portions of the myocardial tissue resulted from cardiac ischemia, a condition in which the myocardium is deprived of adequate oxygen supply and metabolite removal due to an interruption in blood supply caused by an occlusion of a blood vessel such as a coronary artery. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure.

Cardiac pacing is applied to treat various cardiac disorders, such as cardiac arrhythmia, heart failure, MI, and cardiac remodeling, by delivering pacing pulses to the heart to restore the heart's normal rhythm and/or control timing of contraction on one or more regions of the heart. However, when the timing and/or intensity of cardiac pacing are inappropriate, cardiac arrhythmia and/or other cardiac disorders may be worsened. A patient may suffer from more than one of such cardiac disorders and may benefit from several types of cardiac pacing therapy modes. Also for safety, effectiveness, and other reasons, a cardiac pacing therapy may be delivered intermittently. Therefore, there is a need for control timing and/or intensity of cardiac pacing in a safe manner when the patient receives a cardiac pacing therapy that includes mode changes and/or intermittent delivery.

SUMMARY

A cardiac pacing system introduces a transitional period when pacing mode changes, such as when pacing starts and stops, or when one or more pacing parameter values change substantially. For each pacing parameter that changes substantially when the pacing mode changes, its value is adjusted incrementally over the transitional period to protect the heart from potentially harmful conditions associated with an abrupt change in the value of that pacing parameter.

In one embodiment, a CRM system includes a pacing output circuit to deliver pacing pulses and a pacing control circuit to control the delivery of the pacing pulses. The delivery of the pacing pulses is controlled using a plurality of pacing parameters according to a current pacing mode. The pacing control circuit includes a memory circuit, a transition timer, and a transitional parameter adjuster. The memory circuit stores one or more pacing algorithms executable by the pacing control circuit. The one or more pacing algorithms each specify one or more pacing modes. The transition timer initiates and times a transitional period during which the current pacing mode changes from a first pacing mode to a second pacing mode. The transitional parameter adjuster incrementally adjusts at least one transitional pacing parameter over the transitional period. The transitional pacing parameter has a first value associated with the first pacing mode and a substantially different second value associated with the second pacing mode.

In one embodiment, a method for operating a CRM system during a pacing mode transition is provided. Pacing pulses are delivered to a heart. The delivery of the pacing pulses is controlled using a plurality of pacing parameters according to a current pacing mode. A transitional period is initiated and timed during which the current pacing mode changes from a first pacing mode to a second pacing mode. At least one transitional pacing parameter is adjusted from a first value to a second value incrementally over the transitional period. The first value is associated with the first pacing mode. The second value is associated with the second pacing mode and substantially different from the first value.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
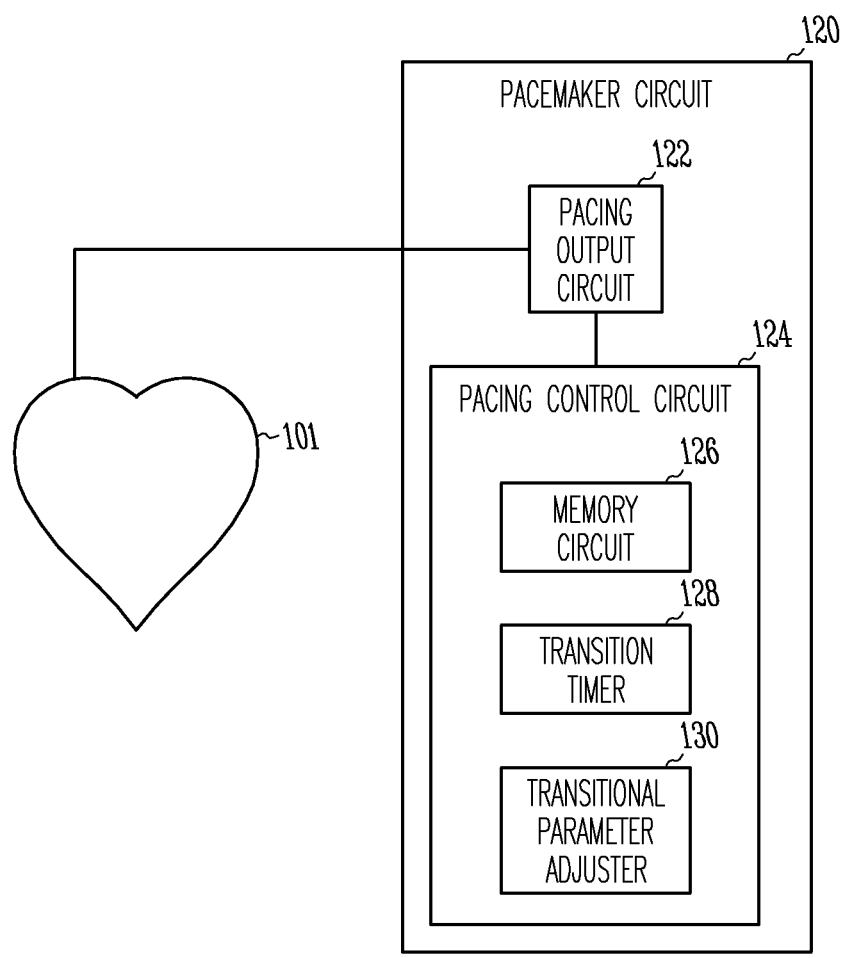
FIG. 1 is a block diagram illustrating an embodiment of a pacemaker circuit coupled to a heart.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses, among other things, a CRM system including a pacemaker that provides transitional periods when pacing mode changes, such as when delivery of pacing pulses starts and stops, or when the one or more pacing parameters controlling the delivery of pacing pulses substantially change. During the transitional period, the cardiac pacing system gradually changes one or more pacing parameters to avoid abrupt transitions that may cause cardiac arrhythmia. In various embodiments, the substantial change in the values of the one or more pacing parameters is required for changing the type or purpose of a pacing therapy.

In one example, the CRM system provides for a cardioprotective pacing therapy that protects the myocardium from injuries associated with ischemia and reperfusion. The delivery of the pacing pulses is controlled by executing a cardioprotective pacing protocol specifying a pacing sequence including alternating pacing and non-pacing periods, or alternating periods of substantially different pacing modes. The cardioprotective pacing protocol specifies pacing parameters selected to create or augment mechanical stress on the myocardium or particular regions of the myocardium. When the cardioprotective pacing therapy is delivered before, during, and after an ischemic or reperfusion event, the result may include reduced infarct size. However, there is a risk for cardiac arrhythmia that may be caused by the changing between the pacing and non-pacing periods or between the periods of substantially different pacing modes. For example, during a pacing period, workload at the pacing site is reduced, while workload at other myocardial regions is increased. An abrupt change in workload at a transition from the non-pacing period to the pacing period, or from the pacing period to the non-pacing period, may induce tachycardia.

The present CRM system provides a transitional period between different pacing modes, including a pacing mode under which no pacing pulse is delivered and other pacing modes corresponding to various types of therapies. Pacing pulses are delivered during the transitional period using incrementally and gradually varying parameters to prevent arrhythmia associated with otherwise abrupt transitions. The transitional period is automatically introduced before a scheduled or otherwise anticipated pacing mode change.

FIG. 1 is a block diagram illustrating an embodiment of a pacemaker circuit 120 coupled to a heart 101. In various embodiments, cardiac pacing is delivered from pacemaker circuit 120 to heart 101 directly through implantable or percutaneous leads with pacing electrodes placed in or about heart 101, or transcutaneously through body-surface electrodes, as further discussed below with reference to FIGS. 7-9.

Pacemaker circuit 120 is part of a CRM system and includes a pacing output circuit 122 and a pacing control circuit 124. Pacing output circuit 122 delivers pacing pulses to heart 101. Pacing control circuit 124 controls the delivery of the pacing pulses using a plurality of pacing parameters according to a current pacing mode. The current pacing mode is selected from a plurality of pacing modes available from pacemaker circuit 120. Pacing control circuit 124 includes a memory circuit 126, a transition timer 128, and a transitional parameter adjuster 130. Memory circuit 126 stores one or more pacing algorithms executable by pacing control circuit 124. The one or more pacing algorithms each specify one or more pacing modes with timing for delivery. Transition timer 128 initiates and times a transitional period during which the current pacing mode changes from a first pacing mode to a second pacing mode. Transitional parameter adjuster 130 incrementally adjusts at least one transitional pacing parameter over the transitional period. The transitional pacing parameter has a first value associated with the first pacing mode and a second value associated with the second pacing mode. The second value is substantially different from the first value such that the risk of cardiac arrhythmia associated with an abrupt change between these two values is considered as being substantial.

The pacing modes are each associated with a unique combination of values for the plurality of parameters controlling the delivery of the pacing pulses. The current pacing mode changes from one pacing mode to another pacing mode when the value of at least one parameter substantially changes. In various embodiments, the current pacing mode changes, for example, when the delivery of pacing starts or stops, when the type of pacing therapy changes (such as changing from a cardiac resynchronization therapy to a cardiac remodeling control therapy), when the value of a parameter substantially changes in response to a substantial change in a sensed parameter, and when a chronic pacing therapy is interrupted to deliver a temporally or intermittent pacing therapy. A specific example of a pacing protocol including scheduled pacing mode changes is a cardioprotective pacing protocol that is further discussed below with reference to FIG. 5.

In various embodiments, pacemaker circuit 120, including its various elements in various embodiments, is implemented using a combination of hardware and software. In various embodiments, each element of pacemaker circuit 120 may be implemented using an application-specific circuit constructed to perform one or more particular functions or a general-purpose circuit programmed to perform such function(s). Such a general-purpose circuit includes, but is not limited to, a microprocessor or a portion thereof, or other programmable logic circuit or a portion thereof. In one embodiment, pacing control circuit 124 is implemented as a microprocessor-based circuit programmed to perform various selected functions discussed in this document.

Figure 2:
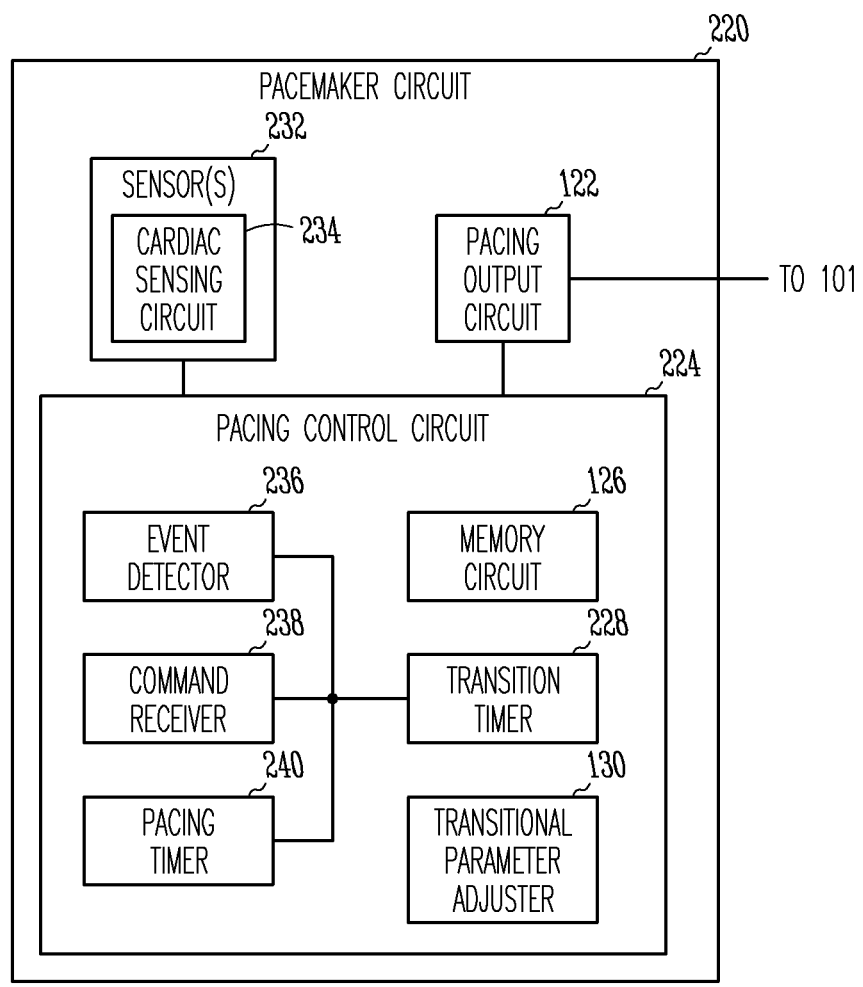
FIG. 2 is a block diagram illustrating another embodiment of the pacemaker circuit.

FIG. 2 is a block diagram illustrating an embodiment of a pacemaker circuit 220, which represents another embodiment of pacemaker circuit 120. Pacemaker circuit 220 includes pacing output circuit 122, one or more sensors 232, and a pacing control circuit 224.

Sensor(s) 232 senses one or more physiological signals. In various embodiments, the one or more physiological signals include one or more signals indicative of cardiovascular condition and/or hemodynamic performance. In various embodiments, the one or more physiological signals include one or more signals indicative a need to start, stop, and adjust the delivery of pacing pulses. In various embodiments, sensor(s) 232 includes a cardiac sensing circuit 234 to sense cardiac signals.

Pacing control circuit 224 represents an embodiment of pacing control circuit 124 and includes memory circuit 126, a transition timer 228, transitional parameter adjuster 130, an event detector 236, a command receiver 238, and a pacing timer 240. Transition timer 228 represents an embodiment of transitional timer 128. In one embodiment, transition timer 228 times a specified time interval as the transitional period. In another embodiment, transition timer 228 counts a specified number of heart beats as the transitional period. In one embodiment, transition timer 228 initiates the transitional period according to a programmed schedule. Pacing timer 240 times pacing periods each being a period during which the pacing pulses are delivered according to a pacing mode of the plurality of pacing modes, and triggers a transitional period when the current pacing period is to be replaced by the next pacing period. The pacing periods are specified in the programmed schedule. In one embodiment, transition timer 228 initiates the transitional period in response to a mode change command. Command receiver 238 receives the mode change command from a user, such as a physician or other caregiver, or from another device. Event detector 236 detects a specified-type mode change event using the sensed one or more physiological signals, and produces the mode change command in response to a detection of the specified-type mode change event.

Examples of transitional pacing parameters include pacing rate, pacing amplitude parameters (pacing voltage and/or pacing pulse width), atrioventricular (AV) delay, interventricular delay, and pacing site parameter specifying sites to which the pacing pulses are delivered. In various embodiments, transitional parameter adjuster 130 incrementally adjusts the at least one transitional pacing parameter from the first value to the second value over the transitional period. In various embodiments, transitional parameter adjuster 130 linearly or curvilinearly adjusts the at least one transitional pacing parameter from the first value to the second value over the transitional period.

In one embodiment, the transitional period is stored in memory circuit 126. In one embodiment, the transitional period is programmable by the user. The length of the transitional period is determined to allow the change of each transitional pacing parameter to be adjusted in a way that is unlikely to induce arrhythmia. Factors to be considered in programming the transitional period include, but are not limited to, the first and second pacing modes, the first and second values of the transitional pacing parameter, and the patient's history of cardiac conditions (e.g., indicative of likeliness that the pacing mode transition will cause arrhythmia in this particular patient).

Figure 3:
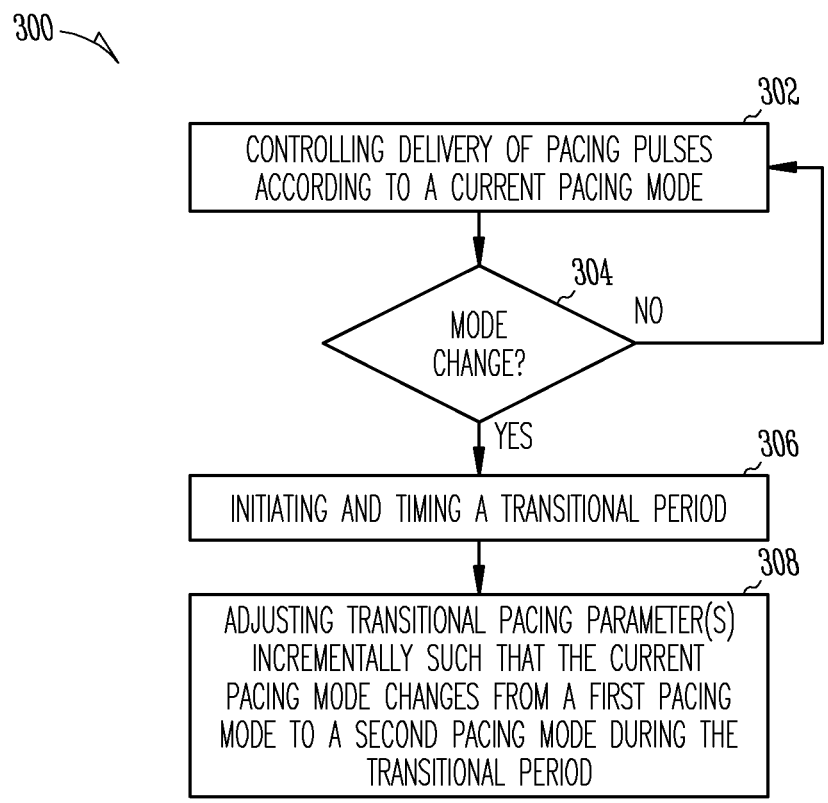
FIG. 3 is a flow chart illustrating an embodiment of a method for safe transition between pacing modes.

FIG. 3 is a flow chart illustrating an embodiment of a method 300 for operating a CRM system. Method 300 provides for safe transition between pacing modes. In one embodiment, pacing control circuit 124 is programmed to perform method 300.

At 302, pacing pulses are delivered to a heart according to a current pacing mode. The current pacing mode is selected from a plurality of pacing modes provided by the CRM system. At 306, if the current pacing mode is to be changed at 304, a transitional period is initiated and timed. At 308, one or more transitional pacing parameters are each adjusted from a first value to a second value incrementally over the transitional period. The first value is associated with a first pacing mode. The second value is associated with a second pacing mode and substantially different from the first value. As a result of the adjustment, the current pacing mode changes from the first pacing mode to the second pacing mode during the transitional period.

Figure 4:
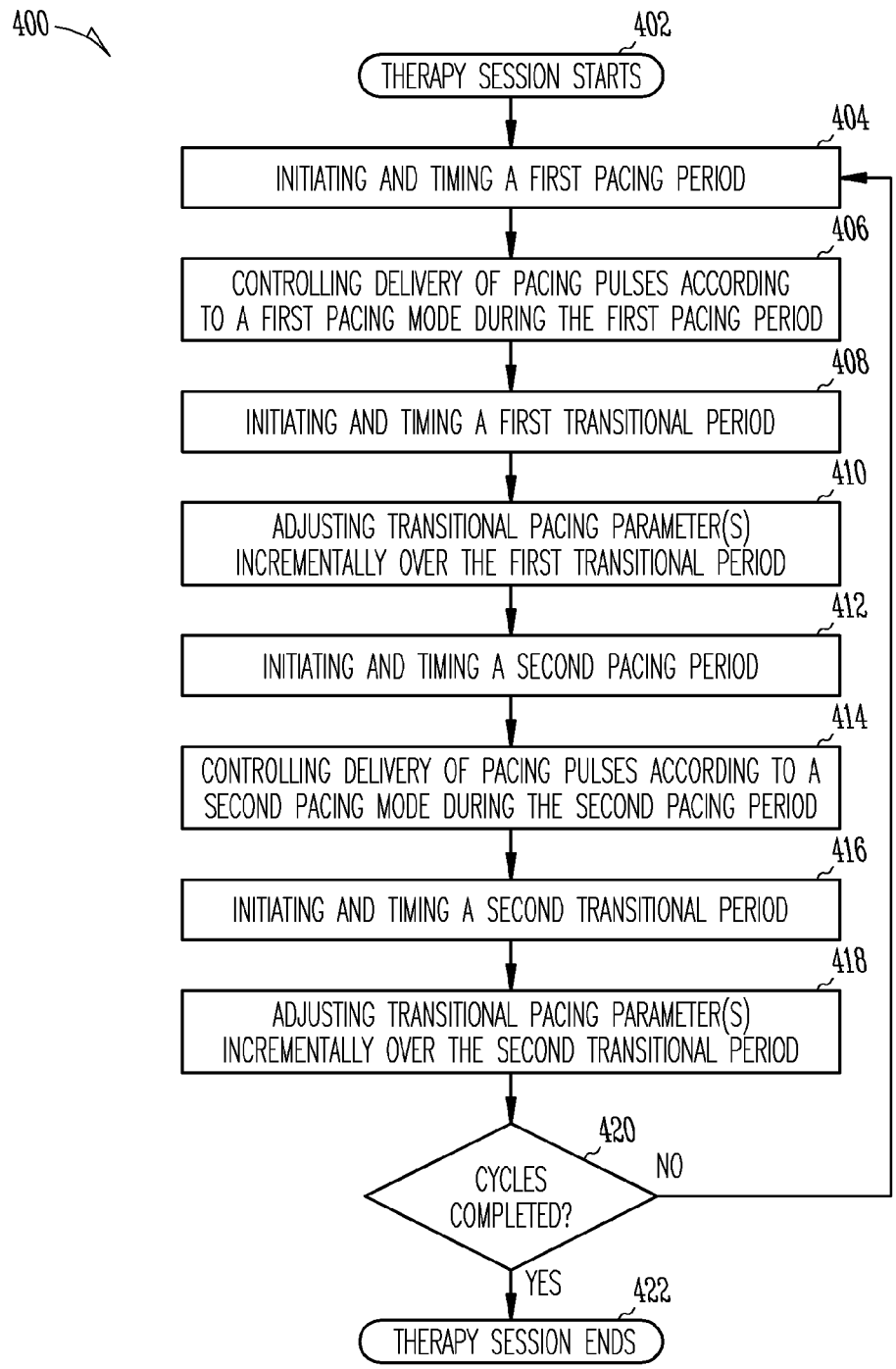
FIG. 4 is a flow chart illustrating an embodiment of a method for executing a pacing protocol with safe transition between pacing modes.

FIG. 4 is a flow chart illustrating an embodiment of a method 400 for operating a CRM system by executing a pacing protocol with safe transition between pacing modes. In one embodiment, pacing control circuit 224 is programmed to perform method 400, as discussed below by way of example, but not by way of limitation. In various embodiments, method 400 is performed by any system capable of being programmed to perform the functions as illustrated in FIG. 4.

At 402, a therapy session starts. For illustrative purposes, the therapy session includes execution of a pacing protocol specifying a pacing sequence including a specified number of cycles of alternating first and second pacing periods. Each cycle includes a first pacing period followed by a second pacing period. The first pacing periods each have a first pacing duration during which the delivery of the pacing pulses is controlled according to the first pacing mode. The second pacing periods each have a second pacing duration during which the delivery of the pacing pulses is controlled according to the second pacing mode. The pacing sequence includes transitions from the first pacing mode to the second pacing mode and transitions from the second pacing mode to the first pacing mode. Pacing control circuit 224 is programmed to control the delivery of pacing pulses by executing the pacing protocol, which is stored in memory circuit 126.

At 404, pacing timer 240 initiates and times the first pacing period. At 406, pacing control circuit 224 controls the delivery of the pacing pulses according to the first pacing mode during the first pacing period. At 408, transition timer 228 initiates and times a first transitional period. In one embodiment, the first transitional period starts at the end of the first pacing period and ends at the beginning of the successive second pacing period. In various other embodiments, the first transitional period overlaps with the first and/or second pacing periods. The first transitional period may (1) start during the first pacing period and end at the beginning of the successive second pacing period, (2) start at the end of the first pacing period and end during the successive second pacing period, and (3) start during the first pacing period and end during the successive second pacing period. At 410, transitional parameter adjustor 130 adjusts one or more transitional pacing parameters incrementally over the first transitional period, such that the value of each transition pacing parameter changes gradually from a first value at the beginning of the first transition period to a second value at the end of the first transition period.

At 412, pacing timer 240 initiates and times the second pacing period. At 414, pacing control circuit 224 controls the delivery of the pacing pulses according to the second pacing mode during the second pacing period. At 416, transition timer 228 initiates and times a second transitional period. In one embodiment, the second transitional period starts at the end of the second pacing period and ends at the beginning of the successive first pacing period. In various other embodiments, the second transitional period overlaps with the first and/or second pacing periods. The second transitional period may (1) start during the second pacing period and end at the beginning of the successive first pacing period, (2) start at the end of the second pacing period and end during the successive first pacing period, and (3) start during the second pacing period and end during the successive first pacing period. At 418, transitional parameter adjustor 130 adjusts one or more transitional pacing parameters incrementally over the second transitional period, such that the value of each transition pacing parameter changes gradually from the second value at the beginning of the second transition period to the first value at the end of the second transition period.

At 420, if the specified number of cycles of the alternating first and second pacing periods is completed, the therapy session ends at 422. Otherwise, pacing control circuit 224 continues executing the pacing protocol by entering the next cycle starting at 404.

The pacing protocol specifying the pacing sequence including alternating first and second pacing periods is discussed for illustrative purposes only. In various embodiments, the pacing protocol may specify a pacing algorithm using two or more pacing modes each corresponding to a pacing period and applied according to a specified pacing delivery schedule. A pacing transitional period is introduced whenever a change between pacing modes may induce cardiac arrhythmia.

Figure 5:
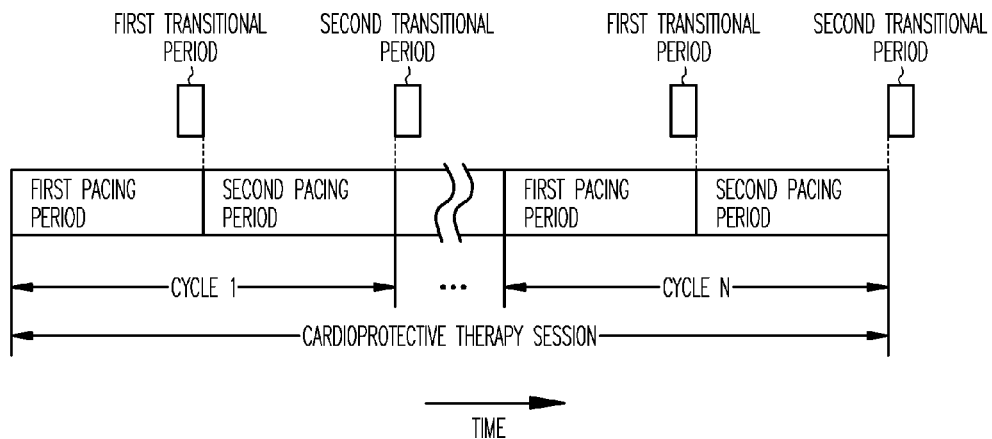
FIG. 5 is a timing diagram illustrating an embodiment of a cardioprotective pacing protocol.

FIG. 5 is a timing diagram illustrating an embodiment of a cardioprotective pacing protocol as a specific example of the pacing protocol executed in method 400 as discussed above with reference to FIG. 4. A cardioprotective pacing protocol is used to deliver a therapy that protects the heart from myocardial injuries resulting from myocardial ischemia or infarction and the subsequent reperfusion. In the illustrated embodiment, the pacing protocol is executed during a cardioprotective therapy session that includes N cycles of alternating first and second pacing periods. Each cycle includes a first pacing period followed by a second pacing period. The first pacing period has a first pacing duration during which the delivery of the pacing pulses is controlled according to a first pacing mode. The second pacing period has a second pacing duration during which the delivery of the pacing pulses is controlled according to the second pacing mode.

In the illustrated embodiment, the first transitional period starts during the first pacing period and ends at a beginning of the successive second pacing period, and the second transitional period starts at an end of the second pacing period and ends during the successive first pacing period. This ensures that the pacing pulses are delivered according to the second pacing mode for the full second pacing period.

In one example of cardioprotective pacing, the first pacing period is a non-pacing period having a first pacing duration during which no pacing pulse is timed to be delivered according to a non-pacing mode, and the second pacing period is a stress augmentation pacing period having a second pacing duration during which the delivery of the pacing pulse is controlled according to a stress augmentation pacing mode. When a pacing pulse is timed to be delivered, it will be delivered unless inhibited by an inhibitory event such as a detected intrinsic cardiac depolarization occurring before the scheduled delivery of the pacing pulse during a cardiac cycle. Under the non-pacing mode according to which no pacing pulse is timed to be delivered, the non-delivery is due to programming rather than inhibition by a detected inhibitory event. Under the stress augmentation pacing mode, pacing pulses are delivered to augment mechanical stress on the myocardium to a level effecting cardioprotection against myocardial injury. In various other embodiments, the stress augmentation pacing mode is a standard or non-standard pacing mode with pacing parameter values selected for the desired level of myocardial stress augmentation according to the patients' needs, conditions, and responses. In one embodiment, the stress augmentation pacing mode is an atrial tracking pacing mode with a relatively short atrioventricular AV delay. In another embodiment, stress augmentation pacing mode is a bradycardia pacing mode with a pacing rate substantially higher than the patient's intrinsic heart rate. In another embodiment, stress augmentation pacing mode is an asynchronous pacing mode with a pacing rate substantially higher than the patient's intrinsic heart rate. In one embodiment, the first pacing duration is substantially equal to the second pacing duration, and the first and second transitional periods are both within the first pacing duration, as illustrated in FIG. 5. This ensures that the pacing pulses are delivered to augment the mechanical stress on the myocardium for the full second pacing duration.

In another example of cardioprotective pacing, the first pacing period is a back-up pacing period having a first pacing duration during which pacing pulses are timed to be delivered according to a back-up pacing mode, and the second pacing period is a stress augmentation pacing period having a second pacing duration during which the delivery of the pacing pulse is controlled according to the stress augmentation pacing mode. In one embodiment, the backup pacing mode is a chronic pacing mode that is substantially different from the stress augmentation pacing mode and applied before and/or after the cardioprotective therapy session. In one embodiment, the back-up pacing mode is an anti-bradycardia pacing mode according to which pacing pulses are timed to be delivered as an anti-bradycardia therapy. In another embodiment, the back-up pacing mode is a cardiac resynchronization mode according to which pacing pulses are timed to be delivered as a cardiac resynchronization therapy (CRT). In another embodiment, the back-up pacing mode is a cardiac remodeling control mode according to which pacing pulses are timed to be delivered as a cardiac remodeling control therapy (RCT). In one embodiment, the first pacing duration is substantially equal to the second pacing duration, and the first and second transitional periods are both within the first pacing duration, as illustrated in FIG. 5. This ensures that the pacing pulses are delivered to augment the mechanical stress on the myocardium for the full second pacing duration.

In various embodiments, the cardioprotective therapy session is applied as an acute pacing preconditioning therapy prior to an anticipated myocardial ischemia or infarction event, an acute pacing postconditioning therapy during or following a myocardial ischemia or infarction event, or a chronic intermittent pacing therapy in response to, or in anticipation of, one or more myocardial ischemia or infarction events. In various embodiments, the number of the cycles N, the first pacing period, and the second pacing period are each programmable. In one embodiment, the first transitional period and the second transitional period are also each programmable. In one embodiment, the cardioprotective therapy session is initiated as an acute preconditioning or postconditioning therapy and includes approximately 3 to 15 cycles of the alternating first and second pacing periods. The first pacing period is in a range of approximately 10 seconds to 60 minutes. The second pacing period is in a range of approximately 10 seconds to 60 minutes. In another embodiment, the cardioprotective therapy session is initiated repeatedly as a chronic intermittent pacing therapy, such as on a periodic basis with a frequency of approximately 1 to 48 sessions per day. Each session includes approximately 2 to 20 cycles of the alternating first and second pacing periods. The first pacing period is in a range of approximately 5 seconds to 120 minutes. The second pacing period is in a range of approximately 5 seconds to 120 minutes.

Figure 6:
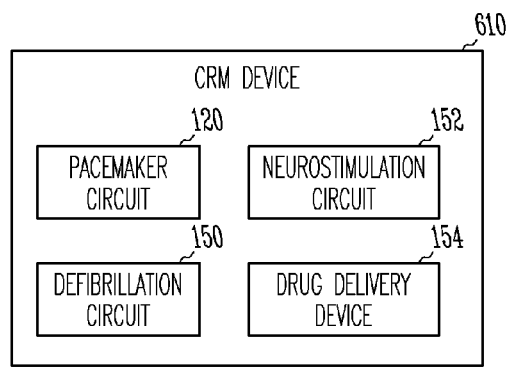
FIG. 6 is a block diagram illustrating an embodiment of a CRM device including the pacemaker circuit.

FIG. 6 is a block diagram illustrating an embodiment of a CRM device 610 including pacemaker circuit 120 (or pacemaker circuit 220 as a specific embodiment of pacemaker circuit 120). In the illustrated embodiment, in addition to pacemaker circuit 120, CRM device 610 includes a defibrillation circuit 150, a neurostimulation circuit 152, and a drug delivery device 154. In various embodiments, in addition to pacemaker circuit 120, CRM device 610 includes any one or more of defibrillation circuit 150, neurostimulation circuit 152, and drug delivery device 154.

Defibrillation circuit 150 delivers cardioversion/defibrillation shocks and controls the delivery of the shocks. This provides additional safety assurance against pacing-induced arrhythmia, in addition to the patient's general need for cardioversion/defibrillation therapy.

Neurostimulation circuit 152 delivers vagal nerve stimulation and controls the delivery of the vagal nerve stimulation to enhance the cardioprotective effect and/or anti-arrhythmic effect of pacing. In one embodiment, neurostimulation circuit 152 delivers the vagal nerve stimulation using neurostimulation parameters selected to enhance the cardioprotective effects of pacing during the cardioprotective therapy session to enhance the cardioprotective effect. In another embodiment, neurostimulation circuit 152 delivers the vagal nerve stimulation using neurostimulation parameters selected to prevent arrhythmia during the first and second transitional periods, thereby enhancing the arrhythmia preventive effect of the transitional periods.

Drug delivery device 154 delivers one or more anti-arrhythmia drugs and controls the delivery of the one or more anti-arrhythmia drugs. In one embodiment, drug delivery device 154 delivers a drug to prevent arrhythmia during the first and second transitional periods, thereby enhancing the arrhythmia preventive effect of the transitional periods.

In various embodiments, CRM device 610 is an implantable medical device coupled to the heart using implantable leads, or an external medical device coupled to the heart using a percutaneous device such as a percutaneous transluminal vascular intervention (PTVI) device and/or body-surface electrodes. Examples of CRM device 610 as an implantable or external medical device are discussed below, with reference to FIGS. 7-9, for illustrative, but not restrictive, purposes.

Figure 7:
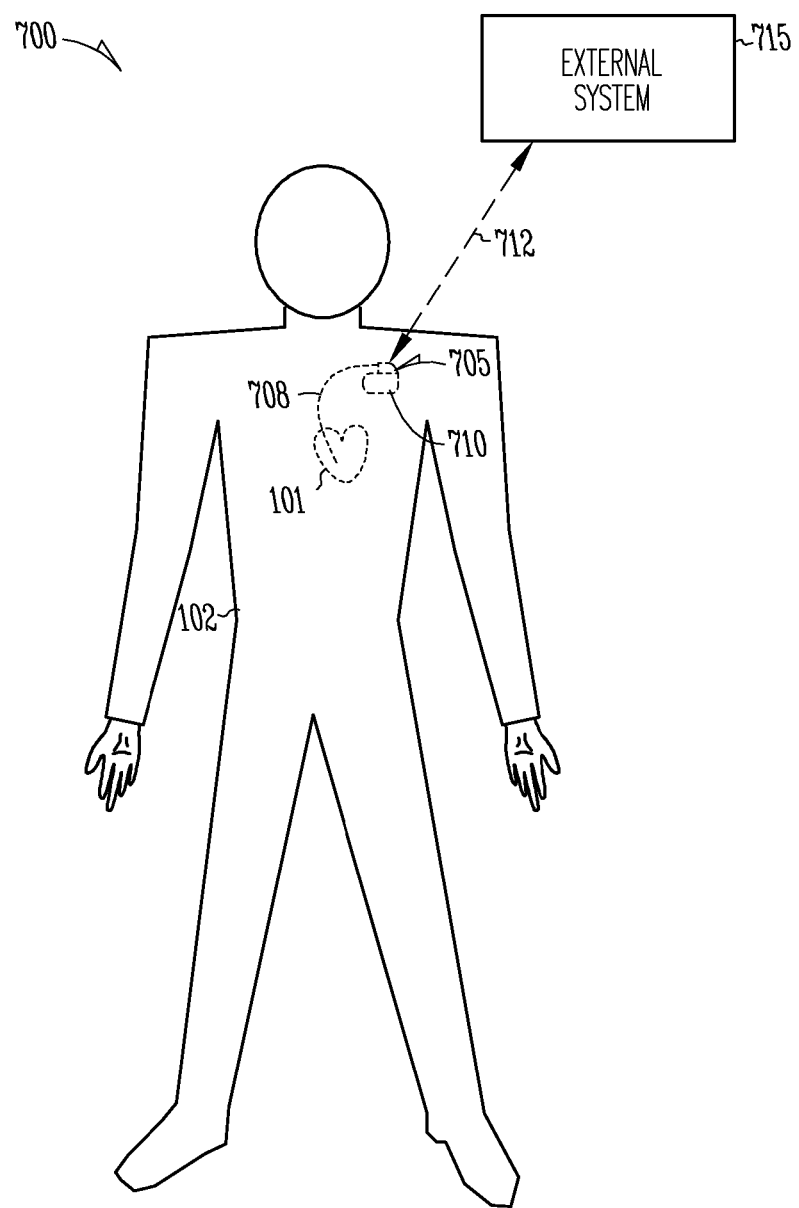
FIG. 7 is an illustration of an embodiment of a CRM system including an implantable CRM device coupled to a heart through one or more implantable leads.

FIG. 7 is an illustration of an embodiment of a CRM system 700 including an implantable CRM device 710 coupled to heart 101 through one or more implantable leads. System 700 includes an implantable system 705, an external system 715, and a telemetry link 712 providing for communication between implantable system 705 and external system 715.

Implantable system 705 includes implantable CRM device 710 and an implantable lead system 708. Implantable CRM device 710 represents an embodiment of CRM device 610, which includes at least pacemaker circuit 120. In various embodiments, implantable CRM device 710 includes one or more of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 7, implantable medical device 710 is implanted in a body 102 having heart 101. In various embodiments, lead system 708 includes implantable leads for sensing physiological signals and delivering pacing pulses, cardioversion/defibrillation shocks, neurostimulation pulses, pharmaceutical agents, biological agents, and/or other types of energy or substance for treating cardiac disorders. In one embodiment, lead system 708 includes one or more implantable pacing-sensing leads each including at least one electrode placed in or about heart 101 for sensing an electrogram and/or delivering pacing pulses. In other embodiments, electrodes placed in body 102 but away from heart 101 are used to sense physiological signals and deliver pacing pulses, cardioversion/defibrillation shocks, neurostimulation pulses, pharmaceutical agents, biological agents, and/or other types of energy or substance for treating cardiac disorders. In a specific embodiment, one or more electrodes are incorporated onto implantable medical device 710 for subcutaneous placement.

External system 715 allows the user such as the physician or other caregiver or a patient to control the operation of implantable CRM device 710 and obtain information acquired by implantable CRM device 710. In one embodiment, external system 715 includes a programmer communicating with implantable medical device 710 bi-directionally via telemetry link 712. In another embodiment, external system 715 is a patient management system including an external device communicating with a remote device through a telecommunication network. The external device is within the vicinity of implantable medical device 710 and communicates with implantable medical device 710 bi-directionally via telemetry link 712. The remote device allows the user to monitor and treat a patient from a distant location.

Telemetry link 712 provides for data transmission from implantable CRM device 710 to external system 715. This includes, for example, transmitting real-time physiological data acquired by implantable CRM device 710, extracting physiological data acquired by and stored in implantable CRM device 710, extracting therapy history data stored in implantable CRM device 710, and extracting data indicating an operational status of implantable CRM device 710 (e.g., battery status and lead impedance). Telemetry link 712 also provides for data transmission from external system 715 to implantable CRM device 710. This includes, for example, programming implantable CRM device 710 to acquire physiological data, programming implantable CRM device 710 to perform at least one self-diagnostic test (such as for a device operational status), programming implantable CRM device 710 to deliver at least one therapy. In one embodiment, the user enters the mode change command using external system 715, which transmits the mode change command to implantable CRM device 710 via telemetry link 712 to trigger a change in the pacing mode.

Figure 8:
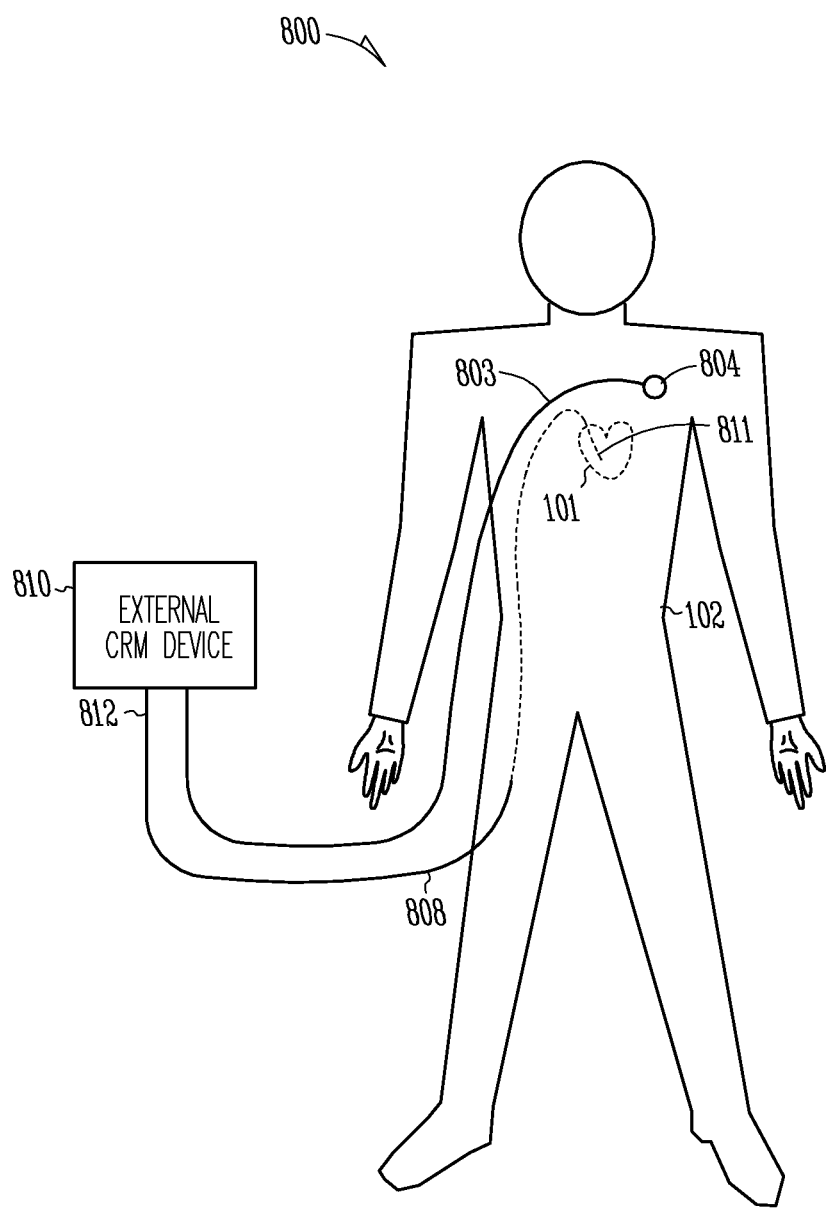
FIG. 8 is an illustration of an embodiment of a CRM system including an external CRM device coupled to a heart through one or more percutaneous devices.

FIG. 8 is an illustration of an embodiment of a CRM system 800 including an external CRM device 810 coupled to heart 101 through one or more percutaneous devices. System 800 includes an external CRM device 810 and a PTVI device 808. When needed, system 800 also includes a reference electrode 804, which is a surface electrode, such as a skin patch electrode, which is connected to external CRM device 810 through a lead 803.

External CRM device 810 represents another embodiment of CRM device 610, which includes at least pacemaker circuit 120. In one embodiment, external CRM device 810 is an external pacemaker such as a pacing system analyzer (PSA). In another embodiment, external CRM device 810 includes an implantable pacemaker adapted for external use. In various embodiments, external CRM device 810 includes a user interface to allow the user to control its operation, including issuing the mode change command that triggers a change in the pacing mode. In various embodiments, system 800 includes one or more of a pacemaker, a cardioverter/defibrillator, a neurostimulator, a drug delivery device, and a biological therapy device, which are each incorporated into external CRM device 810 or physically separate from external CRM device 810 and coupled to body 102 through PTVI device 808 or other leads or catheters.

PTVI device 808 is used during a revascularization procedure and includes a distal end portion 811 for intravascular placement and a proximal end portion 812 for connection to external CRM device 810. Proximal end portion 812 also includes various connectors and other structures allowing manipulation of PTVI device 808 including the percutaneous transluminal insertion of the device and operation of an angioplasty device at distal end 811. In one embodiment, PTVI device 808 is a percutaneous transluminal coronary angioplasty (PTCA) device used in a PTCA procedure. During the PTCA procedure, an opening is made on a femoral artery in body 102. PTVI device 808 is inserted into the femoral artery and advanced to the aorta and then to a coronary artery that narrowed or blocked. The angioplasty device at distal end 811 is then used to open up the blocked coronary artery. Distal end portion 811 of PTVI device 808 includes one or more pacing electrodes to allow pacing pulses to be delivered to heart 101 during the PTCA procedure. In one embodiment, pacing pulses are delivered through two pacing electrodes on distal end portion 811 of PTVI device 808. In another embodiment, pacing pulses are delivered through a pacing electrode on distal end portion 811 of PTVI device 808 and surface electrode 804 functioning as the return electrode for pacing.

Figure 9:
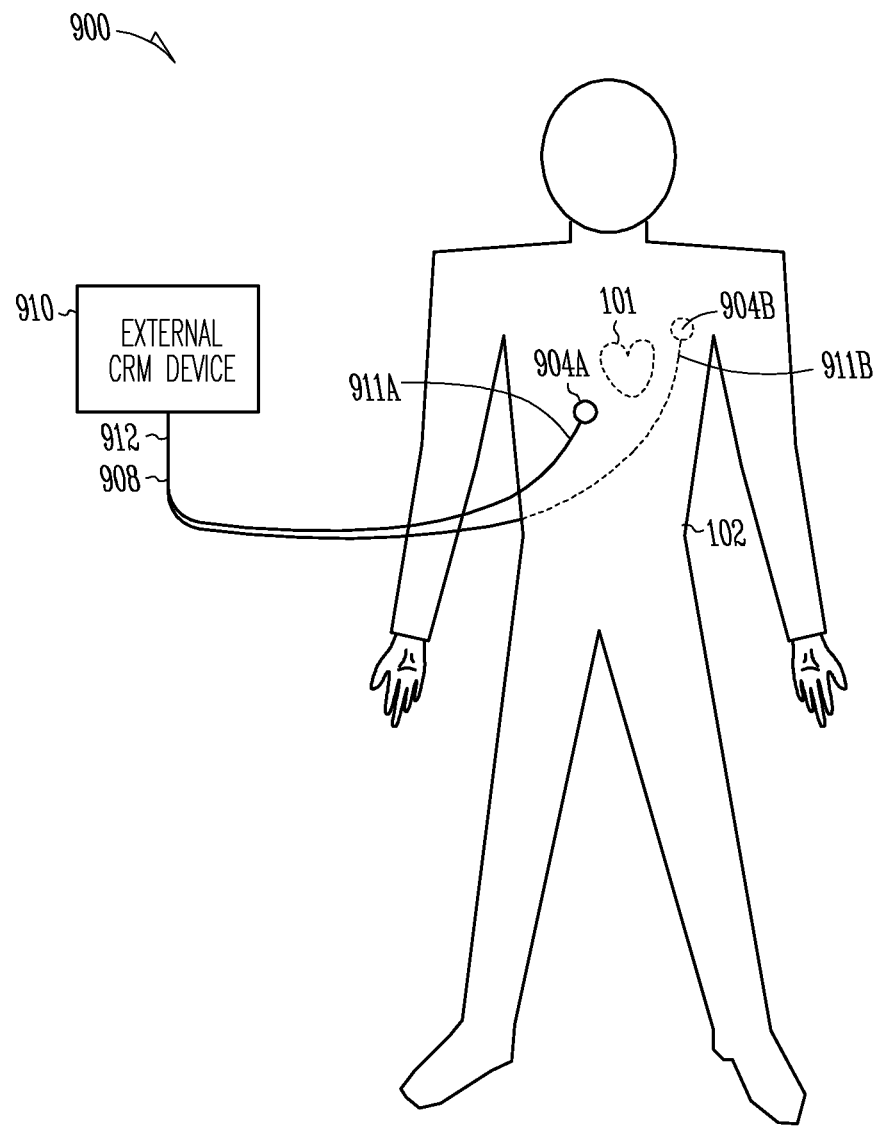
FIG. 9 is an illustration of an embodiment of a CRM system including an external CRM device coupled to a heart through body-surface electrodes.

FIG. 9 is an illustration of an embodiment of a CRM system including an external CRM device 900 coupled to heart 101 through body-surface electrodes and tissue of body 102. System 900 is an external, non-invasive system that includes an external CRM device 910, body-surface electrodes 904A-B, and a cable 908 providing for electrical connections between external CRM device 910 and electrodes 904A-B.

External CRM device 910 represents another embodiment of CRM device 610, which includes at least pacemaker circuit 120. External CRM device 910 is capable of producing pacing pulses that captures heart 101 when delivering transcutaneously through electrodes 904A-B. In various embodiments, external CRM device 910 includes a user interface to allow the user to control its operation, including issuing the mode change command that triggers a change in the pacing mode. In various embodiments, system 900 includes one or more of a pacemaker, a cardioverter/defibrillator, neurostimulator, a drug delivery device, and a biological therapy device, which are each incorporated into external CRM device 910 or physically separate from external CRM device 910 and coupled to body 102 via various leads, catheters, and/or body surface devices. In one embodiment, external CRM device 910 includes an automatic external defibrillator (AED) with pacing capability. Thus, system 900 is capable of providing for non-invasive, transcutaneous delivery of cardioprotective pacing and defibrillation therapies.

In the illustrated embodiment, body-surface electrodes are attached onto body 102 such that transthoracic pacing is delivered with heart 101 in the path of pacing current. In various embodiments, system 900 includes any number of body-surface electrodes needed for delivering the pacing pulses. In one embodiment, the body-surface electrodes are each an adhesive pad electrode. Cable 908 includes a proximal end 912 to be connected to external CRM device 910 and distal end portions 911A-B to be connected to body-surface electrodes 904A-B, respectively.

In one embodiment, system 900 is used to deliver the cardioprotective pacing therapy when a percutaneous or implantable stimulation system is not timely available or not suitable for the patient. For example, if prompt delivery of the cardioprotective pacing therapy is beneficial to the patient, system 900 is used when the patient is in an ambulance, or in an emergency room or catheterization laboratory waiting for a revascularization procedure.

It is to be understood that the above detailed description, including the various examples of devices, therapies, and pacing modes, is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management system for pacing a heart in a living body, the system comprising:
   a pacing output circuit adapted to deliver pacing pulses; and
   a pacing control circuit coupled to the pacing output circuit and adapted to control the delivery of the pacing pulses using a plurality of pacing parameters according to a current pacing mode of a plurality of pacing modes, the pacing control circuit including:
      a memory circuit storing one or more pacing algorithms each specifying one or more pacing modes of the plurality of pacing modes and a transitional period during which the current pacing mode changes from a first pacing mode of the plurality of pacing modes to a second pacing mode of the plurality of pacing modes, the one or more pacing algorithms executable by the pacing control circuit, the transitional period specified as a time interval or a number of heart beats;
      a transition timer programmed to initiate and time the stored transitional period; and
      a transitional parameter adjuster adapted to incrementally adjust at least one transitional pacing parameter of the plurality of pacing parameters from a first value to a second value over the transitional period, the first value associated with the first pacing mode, the second value associated with the second pacing mode and substantially different from the first value.

2. The system of claim 1, wherein the transition tinier is programmed to time the specified time interval as the transitional period.

3. The system of claim 1, wherein the transition timer is programmed to count the specified number of heart beats as the transitional period.

4. The system of claim 1, wherein the transition timer is programmed to initiate the transitional period according to a programmed schedule, and comprising a pacing timer programmed to time pacing periods each being a period during which the pacing pulses are delivered according to a pacing mode of the plurality of pacing modes, the pacing periods specified in the programmed schedule.

5. The system of claim 1, comprising:
one or more sensors adapted to sense one or more physiological signals; and
an event detector adapted to detect a specified-type mode change event using the sensed one or more physiological signals and produce a mode change command in response to a detection of the specified-type mode change event,
and wherein the transition timer is adapted to initiate the transitional period in response to the mode change command.

6. The system of claim 1, wherein:
the pacing control circuit is programmed to control the delivery of the pacing pulses by executing a pacing protocol specifying a pacing sequence including alternating first and second pacing periods, the first pacing periods each having a first pacing duration during which the delivery of the pacing pulses is timed according to the first pacing mode, the second pacing periods each including a second duration during which the delivery of the pacing pulses is timed according to the second pacing mode;
the memory circuit stores the pacing protocol;
the transition timer is programmed to initiate and end a first transitional period during which the current pacing mode changes from the first pacing mode to the second pacing mode and a second transitional period during which the current pacing mode changes from the second pacing mode to the first pacing mode; and
the transitional parameter adjustor is programmed to incrementally adjust the at least one transitional pacing parameter such that the value changes gradually from the first value to the second value over the first transitional period, and from the second value to the first value over the second transitional period.

7. The system of claim 6, wherein the pacing protocol is a cardioprotective pacing protocol, and the second pacing periods are each a stress augmentation pacing period during which the delivery of the pacing pulses is controlled according to a stress augmentation pacing mode adapted to augment mechanical stress on the heart to a level effecting cardioprotection against myocardial injury using the pacing pulses.

8. The system of claim 6, wherein the transition timer is programmed to initiate each of the first transitional periods during one of the first pacing periods and end the each of the first transitional periods at a beginning of a successive second pacing period of the second pacing periods and to initiate the each of the second transitional periods at an end of one of the second pacing periods and end the each of the second transitional periods during a successive first pacing period of the first pacing periods.

9. The system of claim 6, wherein the first pacing periods are each a non-pacing period during which no pacing pulse is timed to be delivered.

10. The system of claim 6, wherein the first pacing periods are each a back-up pacing period during which the delivery of the pacing pulse is controlled according to a back-up pacing mode substantially different from the stress augmentation pacing mode.

11. The system of claim 1, comprising a neurostimulation circuit adapted to deliver vagal nerve stimulation and programmed to control the delivery of the vagal nerve stimulation using neurostimulation parameters selected for anti-arrhythmic effect during the transitional period.

12. The system of claim 1, comprising a drug delivery device programmed to deliver one or more anti-arrhythmia drugs during the transitional period.

13. A method for operating a cardiac rhythm management system, the method comprising:
storing a transitional period specified as a time interval or a number of heart beats;
delivering pacing pulses to a heart;
controlling the delivery of the pacing pulses using a plurality of pacing parameters according to a current pacing mode of a plurality of pacing modes;
initiating and timing the stored transitional period during which the current pacing mode changes from a first pacing mode of the plurality of pacing modes to a second pacing mode of the plurality of pacing modes; and
adjusting at least one transitional pacing parameter of the plurality of pacing parameters from a first value to a second value incrementally over the transitional period, the first value associated with the first pacing mode, the second value associated with the second pacing mode and substantially different from the first value.

14. The method of claim 13, wherein initiating the transitional period comprises initiating the transitional period according to a programmed schedule.

15. The method of claim 13, wherein initiating the transitional period comprises:
sensing one or more physiological signals;
detecting an event indicative a need to start, stop, and adjust the delivery of pacing pulses; and
initiating the transitional period in response to the detection of the event.

16. The method of claim 13, wherein initiating the transitional period comprises initiating the transitional period in response to a mode change command issued by a user.

17. The method of claim 13, wherein adjusting the at least one transitional pacing parameter comprises adjusting at least one of a pacing rate, a pacing amplitude, an atrioventricular pacing delay, and a pacing site parameter specifying one or more sites to which the pacing pulses are delivered.

18. The method of claim 13, wherein:
controlling the delivery of the pacing pulses comprises executing a pacing protocol specifying a pacing sequence including alternating first and second pacing periods, the first pacing periods each having a first pacing duration during which the delivery of the pacing pulses is timed according to the first pacing mode, the second pacing periods each including a second duration during which the delivery of the pacing pulses is timed according to the second pacing mode;
initiating and ending the transitional period comprises initiating and ending a first transitional period during which the current pacing mode changes from the first pacing mode to the second pacing mode and a second transitional period during which the current pacing mode changes from the second pacing mode to the first pacing mode; and
adjusting the at least one transitional pacing parameter comprises adjusting the at least one transitional pacing parameter incrementally from the first value to the second value during the first transitional period and adjusting the at least one transitional pacing parameter incrementally from the second value to the first value during the second transitional period.

19. The method of claim 18, wherein the pacing protocol is a cardioprotective pacing protocol, and the second pacing periods are each a stress augmentation pacing period during which the delivery of the pacing pulses is controlled according to a stress augmentation pacing mode adapted to augment mechanical stress on the heart to a level effecting cardioprotection against myocardial injury using the pacing pulses.

20. The method of claim 19, wherein initiating and ending the first transitional period comprises:
   initiating each of the first transitional periods during one of the first pacing periods and ending the each of the first transitional periods at a beginning of a successive second pacing period of the second pacing periods; and
   initiating each of the second transitional periods at an end of one of the second pacing periods and ending the each of the second transitional periods during one of a successive first pacing period of the first pacing periods.

21. The method of claim 19, wherein the first pacing periods are each a non-pacing period during which no pacing pulse is timed to be delivered.

22. The method of claim 19, wherein the first pacing periods are each a back-up pacing period during which the delivery of the pacing pulse is controlled according to a back-up pacing mode substantially different from the stress augmentation pacing mode.

\* \* \* \* \*